United States Patent [19]

Alley, III et al.

[11] 4,164,944

[45] Aug. 21, 1979

[54] DIGITAL MEANS FOR NON-INVASIVELY CONTROLLING THE PARAMETERS OF AN IMPLANTABLE HEART PACER

[75] Inventors: Lawrence E. Alley, III, North Easton; Richard P. Lydick, Chelmsford; Robert E. Stanley, Roslindale, all of Mass.

[73] Assignee: ARCO Medical Products Company, Leechburg, Pa.

[21] Appl. No.: 795,252

[22] Filed: May 9, 1977

[51] Int. Cl.² ............................................. A61N 1/36
[52] U.S. Cl. ............................................ 128/419 PG
[58] Field of Search ....... 128/419 F, 419 PG, 419 PS, 128/419 PT, 421, 422, 423

[56] References Cited

U.S. PATENT DOCUMENTS

| | | | |
|---|---|---|---|
| 3,805,796 | 4/1974 | Terry, Jr. et al. | 128/419 PG |
| 3,830,242 | 8/1974 | Greatbatch | 128/419 PT |
| 4,049,004 | 9/1977 | Walters | 128/419 PG |

*Primary Examiner*—William E. Kamm
*Attorney, Agent, or Firm*—John C. Martin, Jr.

[57] ABSTRACT

A heart pacer employing a digital parameter controlling circuit is controlled by externally transmitted magnetic pulses of width corresponding to the desired ultimate parameter controlling signal. In the embodiment shown, a magnetic pulse of width about 5.1 milliseconds corresponds to a digital "0", and a pulse of about 20.5 milliseconds corresponds to a digital "1". Circuits for generating and transmitting the pulses as well as for receiving and controlling the pacer parameters in accordance with the pulses are shown.

15 Claims, 10 Drawing Figures

DIGITAL MEANS FOR NON-INVASIVELY CONTROLLING THE PARAMETERS OF AN IMPLANTABLE HEART PACER

BACKGROUND OF THE INVENTION

1. Field of the Invention

This invention relates to improvements in digital circuits for remotely controlling the parameters of fully implantable heart pacers.

2. Description of the Prior Art

Recently, digital technology has been becoming of interest for use in heart pacers, as the cost of integrated circuit packages has dramatically decreased, and the number of available and reliable circuits has risen. An entirely digital heart pacer is shown, for example, by U.S. Pat. No. 3,557,796.

After the appearace of such digital circuits, heart pacer control circuits were advanced which enabled the parameters of the pacer to be remotely, non-invasively controlled. U.S. Pat. No. 3,805,796, for instance, provides a digital counter which counts the number of externally transmitted magnetic pulses. The counter controls bilateral switches which vary the biasing or currents of selected parameter controlling transistors.

In U.S. Pat. No. 3,833,005, a number of pulses are impressed upon an r-f signal transmitted to the implanted pacer where they are counted and stored in a counter for comparison with a repeating, resettable counter.

In none of the prior art circuits known to applicant, however, is the program or parameter controlling information directly sent or transmitted to the pacer. That is, in the prior art, the number of pulses sent is converted to a binary parameter controlling signal, rather than transmitting the binary controlling signal initially.

SUMMARY OF THE INVENTION

In light of the above, it is, therefore, an object of the invention to provide a circuit for providing control logic states to an associated fully implantable heart pacer of the type in which the operating parameters are variable in correspondence to pre-assigned control logic states applied thereto.

It is another object of the invention to provide a heart pacer parameter control circuit as aforesaid in which the control logic states are rapidly established within the control logic states providing circuit from a transmitter spaced from the pacer at a location external to a patient within whom the pacer may be implanted.

It is yet another object of the invention to provide a heart pacer parameter control circuit in which a number of control logic states are established by externally generated magnetic pulses.

It is still another object of the invention to provide a heart pacer parameter control circuit in which the logic state of each of the control logic states is determined by the width of an externally generated magnetic pulse.

It is still yet another object of the invention to provide a heart pacer parameter control circuit in which the number of externally generated magnetic pulses which determine the control logic states is counted, only after the correct count of which are the control logic states decoded or registered to control the parameters of the heart pacer.

It is still yet another object of the invention to provide a heart pacer parameter control circuit which includes an access code recognition requirement by which a predetermined sequence of an initial few of the magnetic pulses must be detected before any parameter controlling data is processed to insure any unintentional changes of the pacer parameters are avoided.

These and other objects, features and advantages will become apparent to those skilled in the art from the following detailed description when read in conjunction with the accompanying drawings and appended claims.

The invention, in one broad aspect, presents a circuit for providing parameter control states to a heart pacer of the type adapted to be implanted within a patient. The circuit includes means for receiving a plurality of pulses of selected widths, generated and applied externally from the patient. Means are provided for producing logic states of 0 or 1 in correspondence with the respective widths of the received pulses. The logic states are registered into means for presenting them as parameter control states to the pacer.

In another aspect of the invention, the externally applied pulses are of first and second widths representing logic 0 and logic 1, respectively. Means are provided within this circuit for receiving the applied pulses. Additionally, means are provided for generating timing pulses having the same period as the received pulses, occurring at a time whereby they coexist with those received pulses representing a logic 1 and do not coexist with those received pulses of narrower width representing a logic 0. The timing pulses are applied to a clock input, and the data pulses are applied to a data input of a register means, whereby the logic states corresponding to the respective widths of the received pulses are registered within the register means.

In still another aspect of the invention, means are provided for similarly processing an initial few of the received pulses as an access code to produce logic states compared by a gate means to enable the remaining received pulses to be processed into the register means for controlling the pacer parameters.

In yet another aspect of the invention, the received pulses are counted to insure that they are not permitted to affect the operating parameters of the pacer until and only unless the total number of the received pulses intended to be processed are received. Additionally, time constraint means are provided within which all of the pulses to be processed must be received prior to the actuation thereof to effect the pacer operating parameters desired.

BRIEF DESCRIPTION OF THE DRAWING

The invention is illustrated in the accompanying drawing, wherein.

Figure 1:
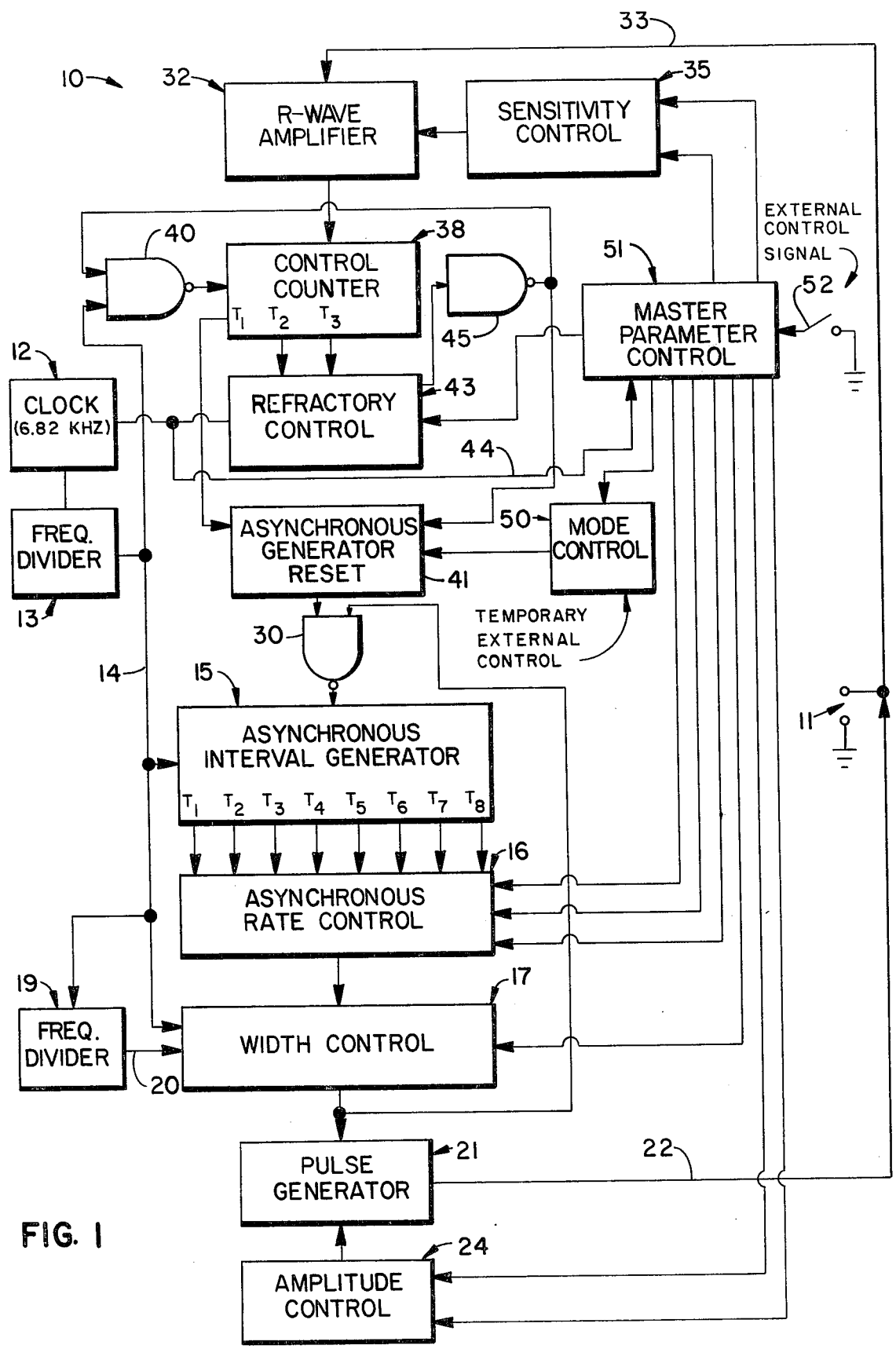
FIG. 1 is a box schematic diagram of a heart pacer in operative association with a parameter control circuit, in accordance with the invention.

In the figures of the drawing, interconnections between the circuits are shown by corresponding letters or letter groups (eg. A—A; CC—CC; FFF—FFF; etc.).

DETAILED DESCRIPTION OF THE PREFERRED EMBODIMENTS

The cardiac pacer, in accordance with a preferred embodiment of the invention is shown in box diagram form in FIG. 1, and is denoted generally by the reference numeral 10. (The various specific electrical circuits of the cardiac pacer in FIG. 1 are illustrated and described below in detail.)

With reference now to FIG. 1, the cardiac pacer 10 receives naturally produced cardiac and other signals from, and supplies stimulation signals to, terminals 11, adapted to be connected to heart electrodes, such connections being well known in the art.

The cardiac pacer 10 operates in conjunction with a digital clock 12, which supplies clock pulses at a frequency of, for example, 6.82 KHz. Pulses from the clock 12 are divided by a frequency divider 13 to be supplied on line 14 to an asynchronous interval generator 15. The asynchronous interval generator 15 has a plurality of outputs T1–T8 each conducted to a respective input of an asynchronous rate control circuit 16. Each of the outputs T1–T8 represents a different asynchronous interval within the range of interest, and the asynchronous rate control 16 selects one of the outputs T1–T8 from the asynchronous interval generator 15, as controlled by a master parameter control circuit 51, below particularly described.

The selected output from the asynchronous interval generator 15 is conducted to a width control circuit 17, which produces an output pulse of selected width, as controlled by the master parameter control 51. This capability is enabled by the clock pulses upon the line 14 being applied directly to the width control 17 and to a frequency divider 19, which produces additional clock pulses upon the line 20 at a submultiple of the frequency of the clock 12, for application to the width control circuit 17, thereby providing two clock pulse frequences from which the various widths of the output pulse can be controlled.

The output pulses from the width control circuit 17 are applied to trigger a pulse generator 21 to produce an output pulse upon output line 22 for delivery to the terminals 11. The amplitude of the pulse generated by the pulse generator 21 is controlled by an amplitude control circuit 24, which, in turn, is also controlled by the master parameter control circuit 51.

The output of the width control circuit 17, in addition to its connection to the pulse generator 21, is conducted via a NAND gate 30 to a resetting terminal of the asynchronous interval generator 15. Thus, when the asynchronous generator 15 reaches a predetermined selected count and produces an output pulse, and the width control circuit 17 generates an output, the asynchronous interval generator is reset to begin counting a subsequent asynchronous interval.

The portion of the cardiac pacer thus described serves as a so-called "fixed rate" pacer, producing pulses asynchronously at a rate controlled by the selected output of the asynchronous interval generator 15. To provide a "demand" pacer capability, a heart signal responsive resetting circuit is provided. This resetting circuit includes an R-wave amplifier 32 having an input connection to terminals 11 from which naturally occurring heart pulses are conducted upon line 33. Other signals, such as stimulation pulses produced by the pulse generator 21 upon the line 22, and electromagnetic interferring noise as may be detected by the heart electrodes or other associated circuitry may also be detected upon the line 33, but is filtered or rejected or initiates a interference or fixed rate mode, as will become apparent below. The sensitivity of the R-wave amplifier 32 is controlled by a sensitivity control circuit 35, which, in turn, is controlled by the master parameter control 51.

The R-wave amplifier 32 produces an output signal upon the detection of a naturally produced R-wave, a stimulation pulse, or an interference signal, for delivery to a control counter 38. The control counter 38 also receives clock pulses from the clock pulse frequency divider 13 via a NAND gate 40, and produces outputs at times $T_1$, $T_2$ and $T_3$, respectively after being reset. The output generated at time $T_1$ is conducted to an asynchronous generator reset circuit 41 which produces an output delivered via NAND gate 30 to reset the count of the asynchronous interval generator 15. Thus, in operation, if an R-wave, a stimulation pulse, or an interference signal is received by the R-wave amplifier 32 prior to the time which a signal appears on a selected output of the asynchronous interval generator 15, the asynchronous interval generator 15 is reset to begin its count anew, in a fashion known in the art as demand operation.

In addition, one of the other of the outputs $T_2$ or $T_3$ of the control counter is selected by a refractory control circuit 43, as controlled by the master parameter circuit 51. The selected output $T_2$ or $T_3$ is connected to an inverting NAND gate 45, for application to the NAND gate 40 controlling the passage of the clock pulses upon the line 14, and to the asynchronous generator reset circuit 41 to produce a state therein allowing the passage of a subsequently produced asynchronous generator reset pulse from the control counter 38. Thus, the refractory circuit functions to produce an "alert state" within the asynchronous generator reset circuit 41 after the control counter 38 has reached a predetermined refractory count determined by the refractory control circuit 43. Upon producing the alert state, a logic state is applied to the input of the NAND gate 40 disabling the passage of the clock pulses upon the line 14, terminating the counting by the control counter 38. Thereafter, the production of an output by the R-wave amplifier 32 produces a pulse resetting the control counter 38 and enabling it to begin its count again. When the count has reached time $T_1$, the asynchronous generator reset 41, previously enabled by the refractory control circuit 43, produces a reset pulse to reset the count of the asynchronous interval generator. Prior to the reaching of the "alert state," however, the pacer is in a "control state" during which the reception of a signal from the R-wave amplifier 32 does not produce an asynchronous interval generator resetting pulse. Instead, the control counter 38 is merely reset to count the preselected refractory period from the beginning.

In addition, a mode control circuit 50 is provided which is controlled by the master parameter control 51. The mode control circuit 50, when operated, disables the operation of the asynchronous generator reset circuit 41, to thereby cause the pacer circuit 10 to operate in a fixed rate mode. Additionally, the mode control 50 can be operated by a temporary external control, such as an electromagnet or the like, to cause the circuit to operate in a fixed rate mode for testing purposes, as is well known in the art.

The master parameter control 51, below described in detail, is programmed via an external control signal applied to a receiving element 52, such as a magnetically activated reed switch or the like, as below described.

As indicated, the cardiac pacer 10, in accordance with the present invention, includes a facility for varying its operating parameters; more particularly, the stimulation pulse width, the stimulation pulse amplitude, the refractory period, the heart signal sensitivity, the mode (i.e. fixed rate or demand) and the asynchronous pulse generation rate. These operating parameters, furthermore, can be varied after the pacer has been implanted into the body of the patient. To facilitate this parameter controlability, the master parameter control circuit 51 is employed. The master parameter control circuit 51 is shown in box diagram form in FIG. 2, and in detail in FIGS. 3A-3C.

As will become apparent, the master parameter control circuit 51 is responsive to an externally applied input from an instruction device or transmitter, below described. The instruction device provides an initial access sequence of electromagnetic pulses followed by a sequence of electromagnetic pulses for determining the operating parameters of the pacer. The control circuit 51 must first recognize the access sequence before the control sequence will be accepted and loaded into the control circuit memory.

Figure 2:
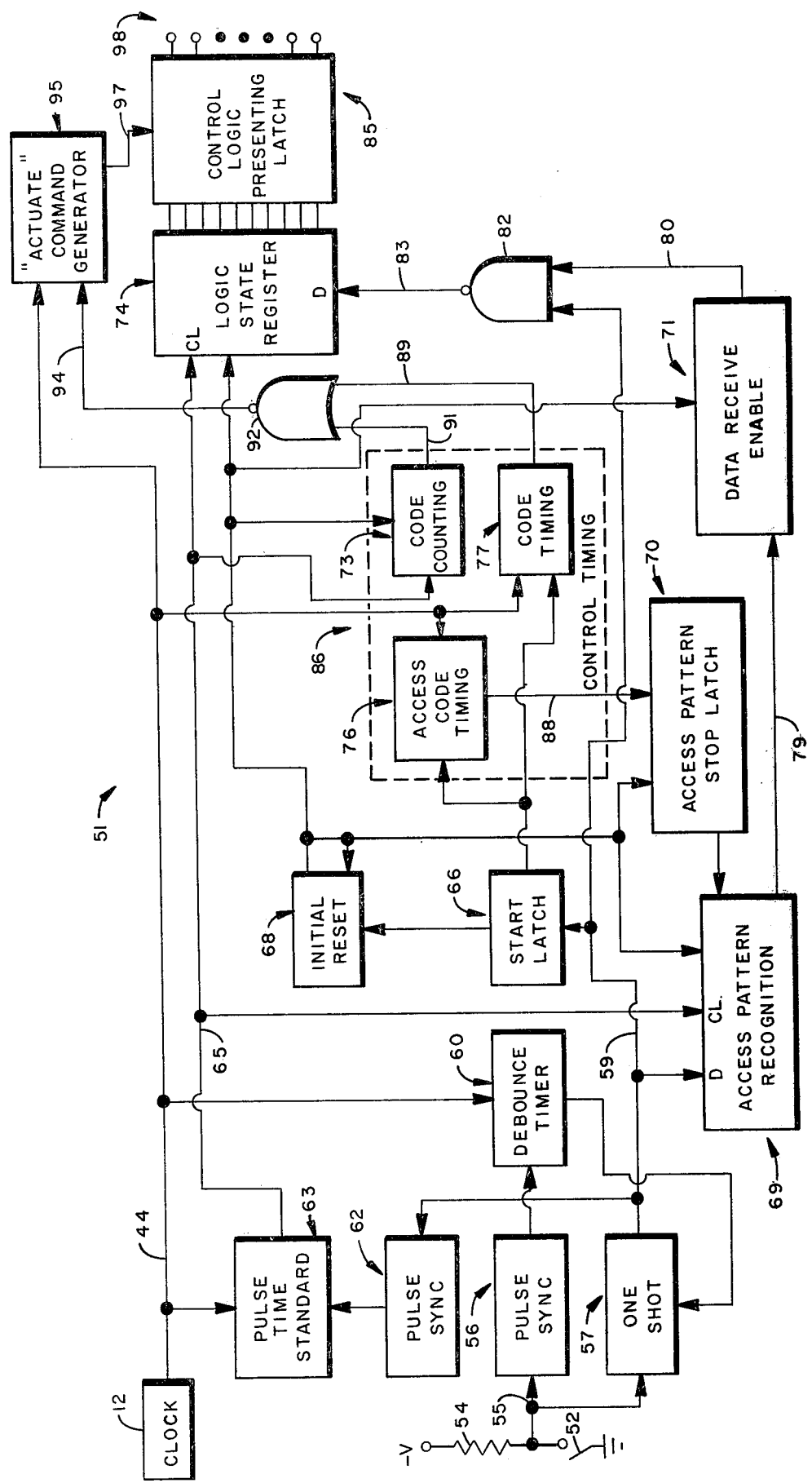
FIG. 2 is a box schematic diagram of the parameter controlling circuit, in accordance with the invention.

More particularly, with reference now to FIG. 2, the master parameter control circuit 51 derives pulses from the clock 12 upon the line 44 to enable the moving and processing of the various pulses and logic states through the master parameter control circuit.

The externally generated and transmitted magnetic pulses are received upon a magnetically actuated reed switch 52. The reed switch 52 is connected in series with a resistor 54 to a low state whereby when the reed switch 52 is closed, pulses are developed across the resistor 54, causing the state upon the input line 55 to change from low to high (ground) state.

The data input line 55 is connected to a pulse sync circuit 56 and to a digital one-shot pulse generator 57. The output of the one-shot pulse generator 57. The output of the one-shot pulse generator 57 is controlled by a debounce timing circuit 60, and is developed upon output data line 59. The debounce timer 60 is actuated by the output from the pulse synchronizing circuit 56 and is controlled by the clock pulses delivered upon line 44. In essence, the debounce timer circuit is a delay circuit which permits the passage of pulses by the one-shot generator 57 only after the expiration of a sufficient time for the magnetic reed switch 52 to complete whatever bouncing it goes through upon closing. Thus, the pulses developed upon the data line 59 represent the pulses produced at the magnetic reed switch 52, except delayed in time by the action of the debounce timer circuit 60.

The output from the one-shot pulse generator 57 upon the data line 59 is delivered to a second pulse synchronizing circuit 62 after which it is conducted to a pulse-time-standard generator 63. The pulse-time-standard generating circuit 63 functions to produce timing pulses a predetermined time after the occurrence of each of the data pulses produced upon the data line 59. The pulses produced by the pulse-time-standard circuit 63 upon the output line 65 serve two purposes, which will be more fully discussed below. Briefly, the first purpose is to enable the data pulse upon the line 59 to be characterized as a "0" or "1" logic state. The second purpose is to provide a signal indicating that a data pulse has been received to permit the data pulses to be counted to insure that the various operating parameters of the pacer are not changed until after all of the transmitted pulses are in fact received.

Upon the appearance of the first data pulse upon the data pulse line 59, a start latch circuit 66 is activated. The start latch circuit 66 activates an initial reset circuit 68, which initializes to a beginning state the access pattern recognition circuit 69, the access pattern stop latch 70, the data receiveenable circuit 71, the code counting circuit 73 and the logic state register 74. The start latch 66 additionally initiates the access code timing circuit 76 and the code timing circuit 77.

The first few of the data pulses received by the magnetic reed switch 52 define an access code which must be received before data pulses can be received to change the pacer parameters. To recognize the access code, the access pattern recognition circuit 69 is provided. The data pulses upon the data line 59 are applied to a data ("D") input and the pulse-time-standard pulses appearing on the line 65 are applied to a clock ("CL") input of the access pattern recognition register 69. As above mentioned, the pulses from the pulse-time-standard circuit 63 appear at a predetermined time after the leading edge of the data pulses. Thus, if the data pulse is in a high state at the time the pulse-time-standard pulse appears at the clock input to the access pattern recognition register, a logic "1" will be entered. If, however, the data pulse has terminated prior to the initiation of the pulse-time-standard pulse, a logic "0" will be registered in the access pattern recognition register.

The access pattern recognition register 69 thus receives the first few, for example five, of the data pulses received by the magnetic reed switch 52, and registers a sequence of logic 1's and 0's. A comparison logic circuit, below described in detail, forms a part of the access pattern recognition circuit 69 to produce an output on the line 79 if and only if the predetermined access code has been properly registered in the access pattern recognition register 69. The "recognize" output upon the line 79 then actuates the data receive enable circuit 71 to produce a state change on its output line 80 to a NAND gate 82 to thereby allow the pulses upon the data line 59 to pass through the NAND gate 82 onto line 83 to a data ("D") input of the logic state register 74.

In a fashion similar to the operation of the above described access pattern recognition register 69, the pulse-time-standard pulses upon the line 65 are applied to a clock ("CL") input of the logic state register 74. Thus, the data pulses upon the line 83 are registered in the logic state register 74 as a logic "0" or a logic "1" state depending on their concurrence with the pulse-time-standard pulses upon the line 65. Upon the completion of the data tramsmission (determined as below described) the logic states within the logic state register 74 are moved to the control logic presenting latch 85 to control the operating parameters of the pacer with which the master parameter control 51 circuit is associated.

Timing of the incoming data pulses is provided by the control timing circuitry 86. The control timing circuitry includes means for timing the access code and the overall code, as well as means for counting the number of magnetic pulses received. Thus, an access code timing circuit 76 is actuated by the start latch 66 (which presents an actuating signal upon the reception of the first magnetic pulse received, as above described). The access code timing circuit 76 receives and counts clock pulses from the line 44 to provide an output upon line 88 to the access pattern stop latch circuit 70 after a period of time within which the access code should be received. After the predetermined time counted by the access code timing circuit 76, the access pattern stop latch 70 is actuated to disable the access pattern recognition circuit 69 so that magnetic pulses received thereafter are ineffective to be recognized as an access code.

Additionally, a code timing circuit 77 is provided which is also initiated by the start latch 66 to receive and count clock pulses upon the line 44 to provide an output upon its output line 89 after a predetermined time within which the entire sequence of magnetic pulses (including the access code pulses) should be received.

Additionally, the pulse-time-standard pulses upon the line 65 are applied to the code counting circuit 73, which provides an output upon its output line 91 at the time a number of pulses corresponding to the total desired number of pulses (including the access code pulses) are received.

The output lines 89 and 91 are connected to the inputs of a NAND gate 92, which produces a state change (to a low state) upon the output line 94 thereof only upon the concurrence of high states upon its input upon lines 89 and 91. The output of the NAND gate 92 is connected to the "actuate" command generator circuit 95 to produce a pulse upon its output line 97 to the control logic presenting latch 85. Thus, in operation, as the data pulses are registered as logic states of 0 and 1 into the logic state register 74, the code counting circuit 73 and code timing circuit 77 are operating. If the desired requisite number of pulses are counted, at the time of the predetermined time, the "actuate" command generator 95 is activated to present a signal upon the output line 97 to transfer the logic states within the logic state register 74 to the control logic presenting latch 85. The logic states, therefore, are then presented upon the various output terminals 98 of the control logic presenting latch 85 to be operational to vary the parameters of the heart pacer with which the master parameter control circuit 51 is associated.

Figure 3A:
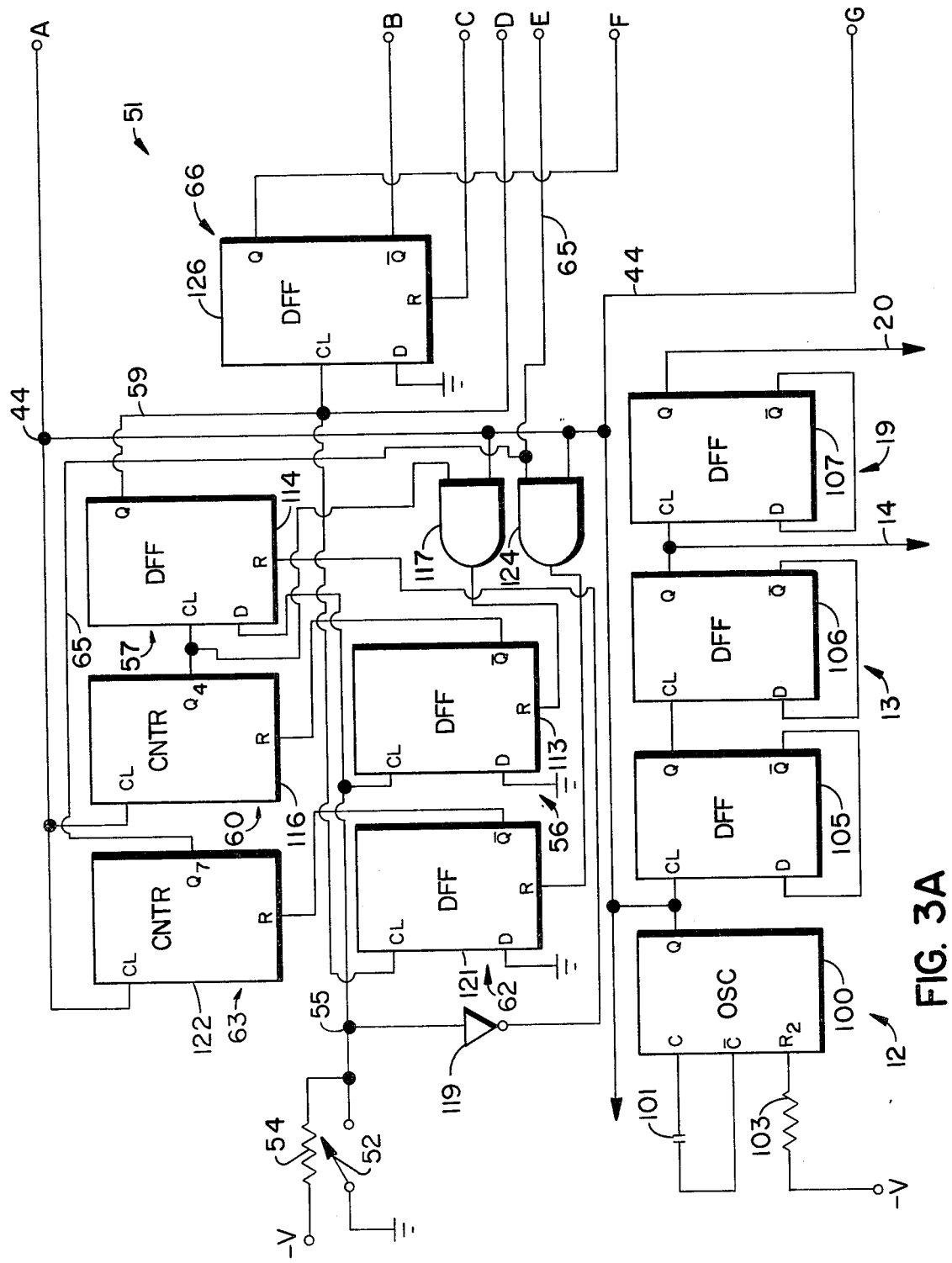
FIGS. 3A–3C are a schematic diagram of the parameter controlling circuit of FIG. 2, and, FIGS. 4A–4E are a schematic diagram of the magnetic pulse generator for remotely controlling the parameter controlling circuit of FIG. 2.
Figure 3B:
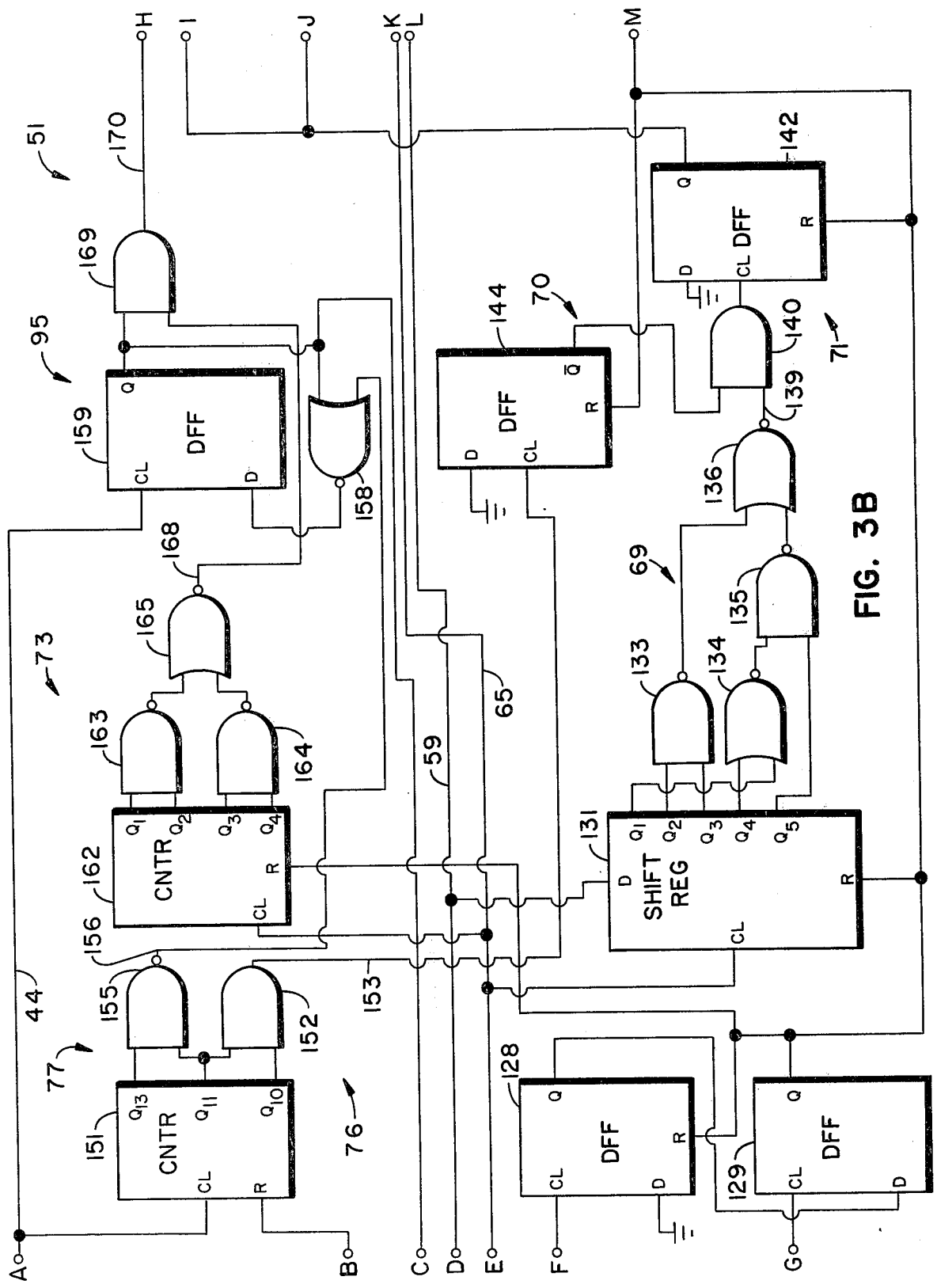
Figure 3C:
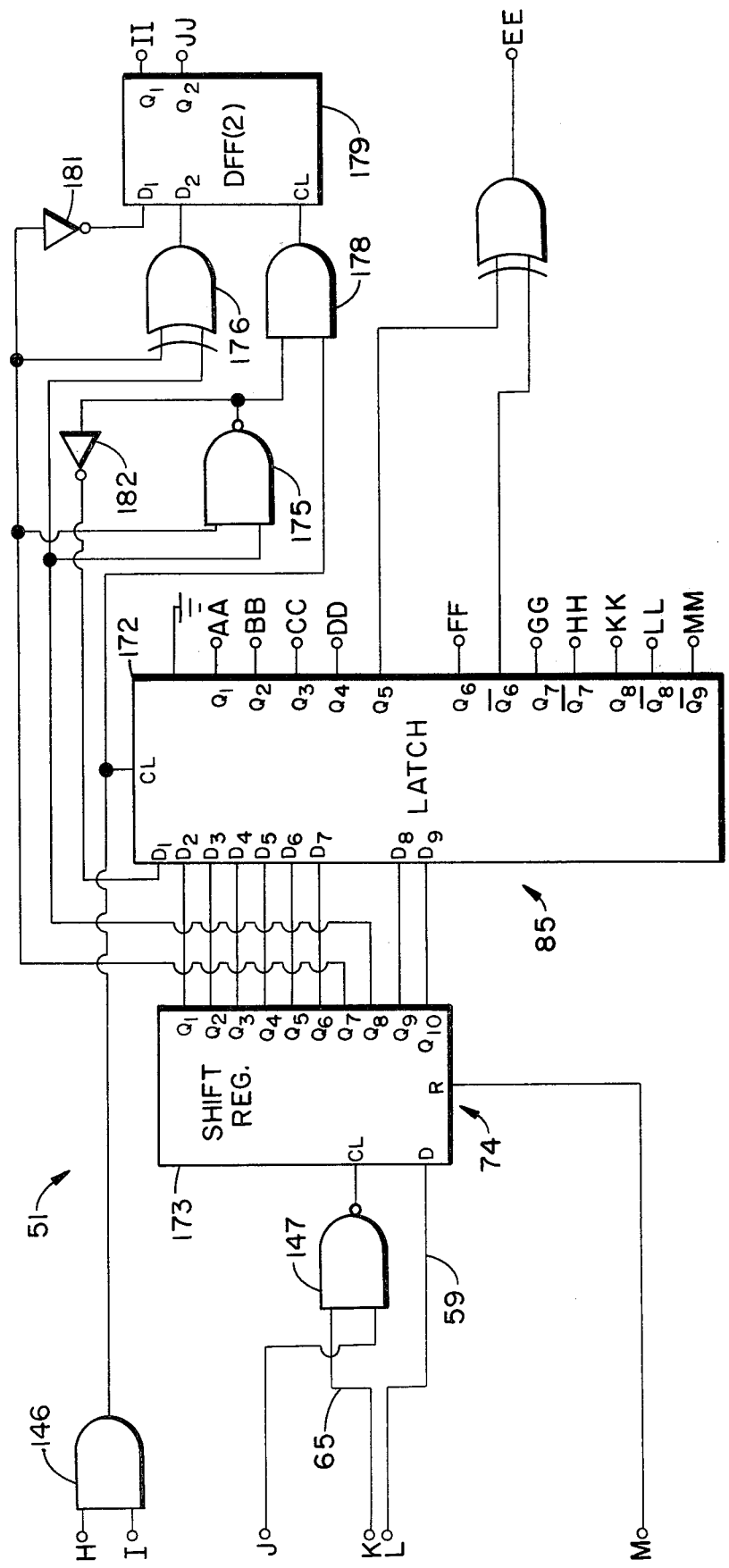

The circuitry of the master parameter control circuit 51 is shown in detail in FIGS. 3A–3C. The interconnections between the various lines of the circuit in FIGS. 3A–3C are denoted by letters A–M, corresponding connections being denoted herein by A—A, B—B, and so forth, and the various block functions shown in FIG. 2, are shown by their respective generic reference numerals.

The clock circuit 12 includes an oscillator 100 having a capacitor 101 connected between its C and $\bar{C}$ terminals, and a resistor 103 connected between the $R_2$ terminal and a low state. The output of the oscillator 100 is obtained from its Q output terminal for delivery to the remainder of the circuit upon line 44. Immediately connected to the oscillator 100 are three D-type master-slave flip-flops 105, 106 and 107. The D-flip-flops 105–107 are connected to serve as the frequency dividers 13 and 19, as shown, to present a first divided frequency upon line 14 and a second divided frequency upon line 20 for use in other portions of the circuit, as shown in FIG. 1, and as will become apparent below.

The pulses from the external instruction device, below described, are received upon the magnetically actuated reed switch 52 for delivery to the pulse sync circuit 56 and the one-shot generator 57. The pulse sync circuit 56 includes a D-type master-slave flip-flop 113 having its clock terminal connected to receive the received pulses from the switch 52. The one-shot pulse generator 57 includes a D-type master-slave flip-flop 114 having its D input terminal connected to receive the received pulses from the switch 52.

The $\bar{Q}$ output of the D flip-flop 113 is connected to the debounce circuit 60, which includes a four stage counter 116. The four stage counter 116 has its reset terminal connected to the $\bar{Q}$ output of the D flip-flop 113 and receives clock pulses upon its clock input from line 44. The terminal $Q_4$ of the counter 116 is connected to the clock input of the D flip-flop 114, and to one input terminal of an AND gate 117. The other input to the AND gate 117 is connected to the clock pulse supply line 44, and the output of the AND gate 117 is connected to the reset terminal of the D flip-flop 113. The reset terminal of the D flip-flop 114 is connected to the magnetic switch 52 by an inverter 119.

The D flip-flop 113 providing the pulse sync, and the counter 116 (and D flip-flop 114) providing the debounce timer operate as follows. When a data pulse appears at the clock input to the D flip-flop 113, the $\bar{Q}$ output changes states from normally high to low (a high state being permanently connected to the D input). The high state, therefore, on the reset terminal of the counter 116 is removed, allowing the counter 116 to count the clock pulses appearing on the line 44. After delay corresponding to the change in state upon the output line $Q_4$, corresponding to the desired debounce delay (1.17 milliseconds in the illustrated embodiment), an output state change upon the output terminal $Q_4$ appears. This state change is applied to the clock terminal of the D flip-flop 114, which will permit the data pulse upon the line 55 to be transferred to the Q output thereof. Additionally, the output upon the $Q_4$ terminal, together with the clock pulses upon the line 44, are compared by the AND gate 117 to reset the D flip-flop 113 to terminate the counting of the counter 116 when the $Q_4$ output and a clock pulse coincide. After the termination of the received data pulse by the magnetic switch 52, a high state is applied by the inverter 119 to reset the D flip-flop 114.

The output derived at the Q terminal of the D flip-flop 114 is connected to the pulse sync circuit 62, which includes a D-type master-slave flip-flop 121. The D terminal of the D flip-flop 121 is connected high, and the clock terminal is connected to the Q terminal of the D flip-flop 114. The $\bar{Q}$ output of the D flip-flop 121 is connected to a reset terminal of a seven stage counter 122 which comprises the pulse time standard circuit 63. The clock input of the counter 122 is connected to the clock pulse supply line 44, and the output is derived at the $Q_7$ terminal. The $Q_7$ terminal together with the clock pulse supply line 44 are connected to the input terminals of an AND gate 124, the output of which is connected to the reset terminal of the D flip-flop 121.

The operation of the pulse standard circuit 63, provided by the seven stage counter 122, is as follows. Upon the appearance of the debounced data pulse upon the terminal Q of the D flip-flop 114, the D flip-flop 121 changes states, to provide a low state at its $\bar{Q}$ output terminal. This low state removes the resetting state upon the reset terminal of the seven stage counter 122, enabling it to count the clock pulses upon its clock input terminal. When the counter 122 reaches the count to produce a state change upon its output terminal $Q_7$ (in about nine milliseconds in the illustrated embodiment), the state or condition upon the output line 63 changes from low to high. This state change is conducted via the AND gate 124 to reset the D flip-flop 121 in preparation for reception of the next succeeding data pulse. The width of the pulses appearing on the line 65, therefore, are the width of the clock pulses, due to the combinational logic of the AND gate 124.

The Q output from the D flip-flop 114 is connected to the start latch circuit 66, which includes a D type master-slave flip-flop 126. The D input of the D flip-flop 126 is tied high, the clock input is connected to the Q output of the D flip-flop 114, and outputs are derived at the Q and $\overline{Q}$ terminals.

The Q output terminal of the D flip-flop 126 is connected to the initial reset circuit 68 (FIG. 3B), which includes two D-type master-slave flip-flops 128 and 129. The Q output of the D flip-flop 126 is connected to the clock input of the D flip-flop 128, and the Q output of the D flip-flop 128 is connected to the D input of the flip-flop 129. The D input terminal of the D flip-flop 128 is connected to a high state, and the Q output terminal of the D flip-flop 129 is connected to the reset terminal of the D flip-flop 128.

The data derived upon the line 59 from the D flip-flop 114 is connected to the access pattern recognition circuit 69, which includes a shift register 131 and four NAND and NOR gates 133-136. The data terminal of the shift register 131 is connected to the data line 59, and the clock input is connected to the output from the pulse time standard counter 122. The various outputs $Q_1$-$Q_5$ of the register 131 are conducted through a network of NAND and NOR gates 133-136. The output from the NAND gate 136 upon the line 139, therefore, changes state only when a predetermined pattern of states exists on the $Q_1$-$Q_5$ terminals of the shift register 131. In the embodiment illustrated, the output upon the line 139 is developed when the states on terminals $Q_1$-$Q_5$ are 10110, respectively. It will be appreciated that any other access sequence desired can be achieved merely by rearranging the order and connections of the NAND and NOR gates 133-136.

Since the data pulses upon the data supply line 59 are of a period defined by the time of closure of the magnetic reed switch 52, modified by the debounce delay, and since the time of occurrence of the clock pulse to the shift register 131 is defined by the time standard counter 122, the states clocked into the shift register 131 will be determined by the pulse width of each individual data pulse. For example, if a data pulse applied to the D input of the shift register 131 terminates prior to the occurrence of the clock pulse defined by the state change of the $Q_7$ output of the counter 122, a zero logic state will be recognized. On the other hand, if the data pulse upon the data line 59 is of sufficient width to still be in existence at the time of the occurrence of the clock pulse upon the shift register 131, it will be recognized as a one. Thus, it can be seen that since the clock pulses upon the shift register 131 are defined by the $Q_7$ output of the counter 122, since the master clock pulses are of 6.82 KHz, the $Q_7$ output of the counter 122 provides a state change after 9.4 milliseconds. Therefore, if a data pulse is of width larger than 9.4 milliseconds, it will be recognized as a high logic state or one. On the other hand, if it is of width less than 9.4 milliseconds, it will be recognized as a low logic state or zero.

The output on the line 139 is applied via an AND gate 140 to the clock terminal of a D-type master-slave flip-flop 142. The D flip-flop 142 serves as the data receive enable circuit 71, and is described below. The other input to the AND gate 140 is derived from the $\overline{Q}$ output terminal of a D-type master-slave flip-flop 144. The D flip-flop 144 provides the access pattern stop latch function, and will also be described below in detail.

The $\overline{Q}$ output of the D flip-flop 142 is normally high for a predetermined time after the initial data pulses are received by the circuit; therefore, the change in state upon the line 139 upon the recognition of the access code within the shift register 131 will effect a clock actuating pulse to the clock input of the D flip-flop 142. The D terminal of the D flip-flop 142 is connected to a high state, and the Q output is connected to an input terminal of an AND gate 146 (FIG. 3C) and to an input terminal of a NAND gate 147 (FIG. 3C) to control the passage of the pulses therethrough. Thus, until the access code defined by the arrangement of the NAND and NOR gates 133-136 upon the $Q_1$-$Q_5$ terminals of the shift register 131 is recognized, no data or other state changes are permitted to pass the AND gate 146 and the NAND gate 147.

As mentioned above, after a time period sufficient for the access code to be loaded into the shift register 131, the search is terminated by the access code timing circuit 76 (FIG. 3B) and the access pattern stop latch 70 (FIG. 3B). The access code timing circuit 76 includes a thirteen stage counter 151, and the access pattern stop latch includes a D flip-flop 144. The thirteen stage counter 151 receives clock pulses upon its clock terminal from the clock pulse supply line 44, and the $\overline{Q}$ output terminal of the D flip-flop 126 (FIG. 3A) is connected to its reset terminal, whereby, upon the actuation of the D flip-flop 126 by the first data pulse received upon the data line 59, the counter 151 is enabled to begin its count. Outputs are derived from the counter 151 upon the $Q_{10}$ and $Q_{11}$ terminals, to be compared by the AND gate 152. Thus, the state seen on the line 153 from the output of the AND gate 152 changes state on the concurrence of high states upon the terminals $Q_{10}$ and $Q_{11}$, which, with a clock frequency of 6.82 KHz of the embodiment herein will occur at about 225 milliseconds after the reception of the first data pulse.

The output from the AND gate 152 is conducted upon the line 153 to the clock input of the D flip-flop 144, mentioned above. The D input of the D flip-flop 144 is connected to a high state, and the $\overline{Q}$ output is connected to an input of the AND gate 140. Thus, after about 225 milliseconds from the reception of the first data pulse, the $\overline{Q}$ output of the D flip-flop 144 changes from high to low states, thereafter disabling the passage of any data states through the AND gate 140. Therefore, if the access code is not recognized upon the terminals $Q_1$-$Q_5$ of the shift register 131 within 225 milliseconds after the reception of the first data pulse, it cannot thereafter be recognized.

The thirteen stage counter 151, in addition to providing the access code timing, additionally provides the total code timing circuit 77. This total timing is derived at the output terminals $Q_{11}$ and $Q_{13}$, which are compared by the NAND gate 155. Thus, the state change on the output line 156 from the NAND gate 155 occurs after the elapse of about 750 milliseconds after the reception of the first data pulse upon the line 59. The output line 156 from the NAND gate 155 is connected to one input of a NOR gate 158. The output of the NOR gate 158 is connected to the input of a D-type master-slave flip-flop 159 which serves as the "actuate" command generator 95. The clock pulses upon the clock pulse supply line 44 are connected to the clock input of the D flip-flop 159, and the Q output terminal is connected to the other input terminal of the NOR gate 158 (the first terminal connection is described above). The Q output of the D flip-flop 159 is also connected to the reset terminal of the D flip-flop 126 to reset it to an initial condition. Therefore, if the data pulses are not completely received by the circuit 51 within 750 milliseconds after the first data pulse is received, the D flip-flop 159 will change states, disabling the passage of any further data pulses which might occur on the data line 59.

In addition to the code timing provided by the counter 151, a code counting circuit 73 is provided including a four stage counter 162, NAND gates 163 and 164, and NOR gate 165. The four stage counter 162 receives pulses at its clock terminal from the $Q_7$ output of the time standard pulse counter 122. The outputs upon the terminals $Q_1$–$Q_4$ are combined by NAND gates 163 and 164 and NOR gate 165. Thus, the output line 168 will change state from low to high upon the concurrence of high states of all of the outputs $Q_1$–$Q_4$. The high concurrence of the outputs $Q_1$–$Q_4$ occurs after fifteen pulses are received. (This corresponds to five pulses defining the data access code sequence and ten pulses defining the desired parameter state change conditions.)

The output upon the line 168 from the NOR gate 165 is connected to one input of an AND gate 169. The other input of the AND gate 169 is connected to the Q output of the D flip-flop 159 which, as above described, changes state after 750 milliseconds from the receipt of the first data pulse. Thus, after the requisite number of data pulses are received, as determined by the counter 162 and the combinational logic used in conjunction therewith, and after the lapse of 750 milliseconds, the state upon the line 170 at the output of the AND gate 169 changes. Since the other input to the AND gate 146 was previously in a high state (assuming the access code has been recognized), as determined by the D flip-flop 142, the state change upon the line 170 is transmitted to a clock terminal of a latch 172, below described in detail.

Concurrently the data upon the data line 59 is connected to a data input of a shift register 173. The pulse time standard developed at the $Q_7$ output of the counter 122 (FIG. 3A) is connected via line 65 through the NAND gate 147 to a clock terminal of the shift register 173. The Q output of the D flip-flop 142 (FIG. 3B) is connected to the other input of the NAND gate 147 to enable the passage of the pulse time standard pulses on line 65 upon the operation of the data receive enable circuit 71.

The outputs of the shift register 173 are developed upon the $Q_1$–$Q_{10}$ terminals. The data is recognized by the shift register 173 in a manner similar to that described with respect to the data shifted into the access pattern recognition shift register 131. That is, if the respective data pulses upon the data line 59 are of width sufficiently large to coincide with the pulse time standard pulses on the line 63, the data is recognized as a high state or logic one. If the respective pulses on the data line, however, are of width sufficiently small whereby they do not coexist with standard pulses, they will be recognized within the shift register 173 as a low state or logic zero.

Consequently, after the data is entirely loaded into the shift register 173, after the desired number of total pulses are received and the requisite time elapsed, the line 170 changes state, thereby clocking the data within the shift register 173 into the latch 172.

To expand the data handling capability of the latch 172, additional logic circuitry is provided, as shown, Thus, the output terminals $Q_7$ and $Q_8$ of the shift register 173 are connected to the input terminals of a NAND gate 175, and to the input terminals of an exclusive OR gate 176. The output of the NAND gate 175 together with the output of the AND gate 146 are connected to the inputs of an AND gate 178, the output of which is connected to a clock input of a dual D-type master-slave flip-flop package 179. The output of the exclusive OR circuit 176 is connected to the $D_2$ input of the flip-flop 179. Additionally, the $Q_7$ output of the shift register 173 is inverted by inverter 181, the output of which is connected to the $D_1$ input of the D flip-flop package 179. The output of the NAND gate 175 additionally is inverted by inverter 182, and connected to the $D_1$ data input of the latch 172. Thus, in addition to the logic states presented at the various output terminals of the latch 172, as denoted by the double letters AA—MM, additional outputs can be achieved by various other logic configurations, as shown.

The logic output states AA—MM can be utilized in conjunction with a heart pacer circuit such as that described and illustrated in U.S. Pat. application No. 663,373, filed Mar. 3, 1976, by applicant Robert A. Walters, entitled IMPLANTABLE DIGITAL CARDIAC PACER HAVING EXTERNALLY SELECTIBLE OPERATING PARAMETERS, and assigned to the assignee hereof. Said patent application is hereby incorporated herein by reference. Other means for utilizing the logic states at the output terminals of the latch 172 to control the operating parameters of the pacer can be employed, such as by the use of bi-lateral switches controlled thereby, as shown in U.S. Pat. No. 3,805,796.

Additionally, although fourteen output states are shown, any number may be used, depending upon the number of operating parameters desired to be controlled, and the number of output states required to control each such parameter.

The circuit for changing and controlling the parameters of the heart pacer above described for use externally to the patient is shown in FIGS. 4A–4E, and is denoted generally by the reference numeral 200.

Figure 4A:
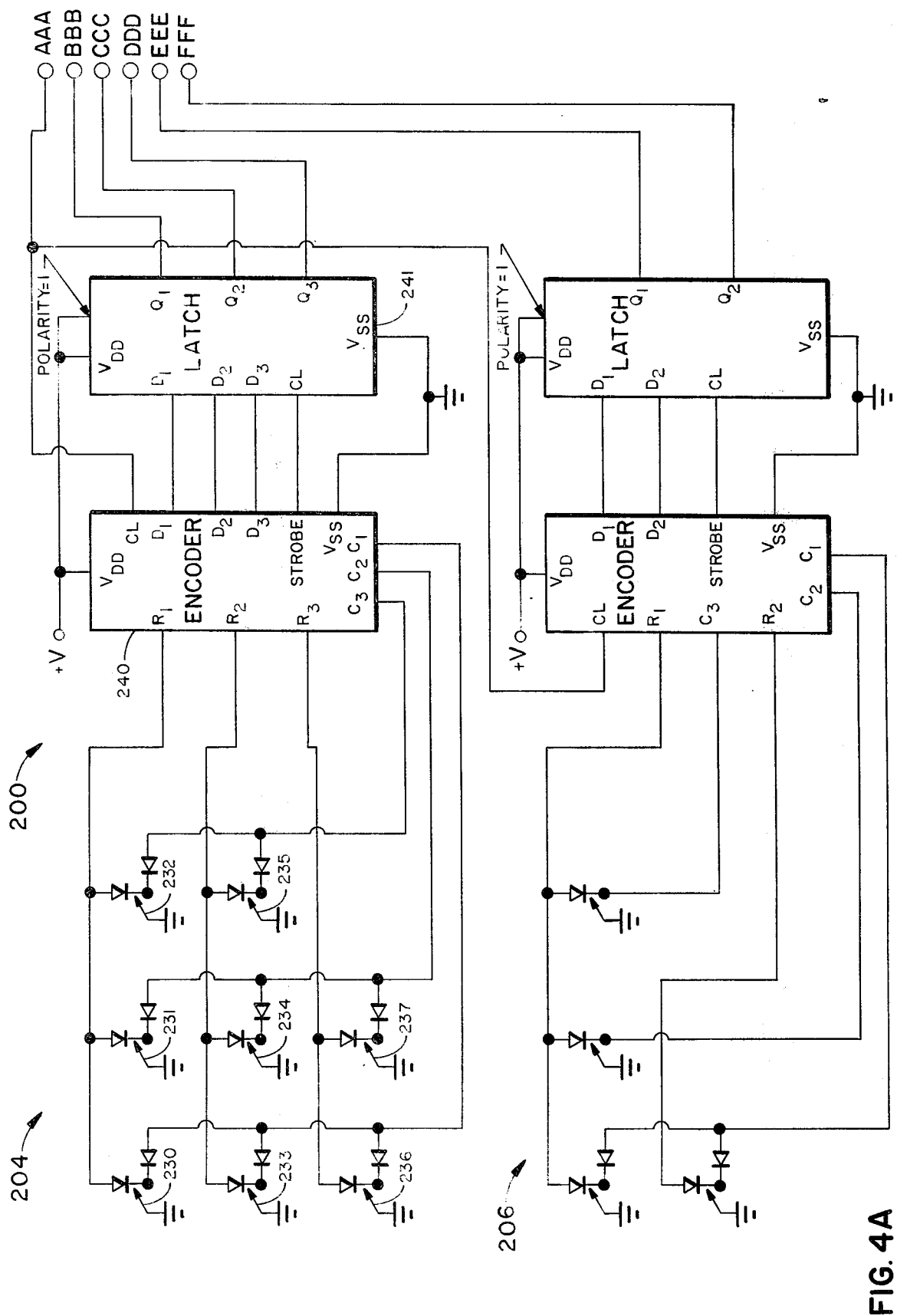
Figure 4B:
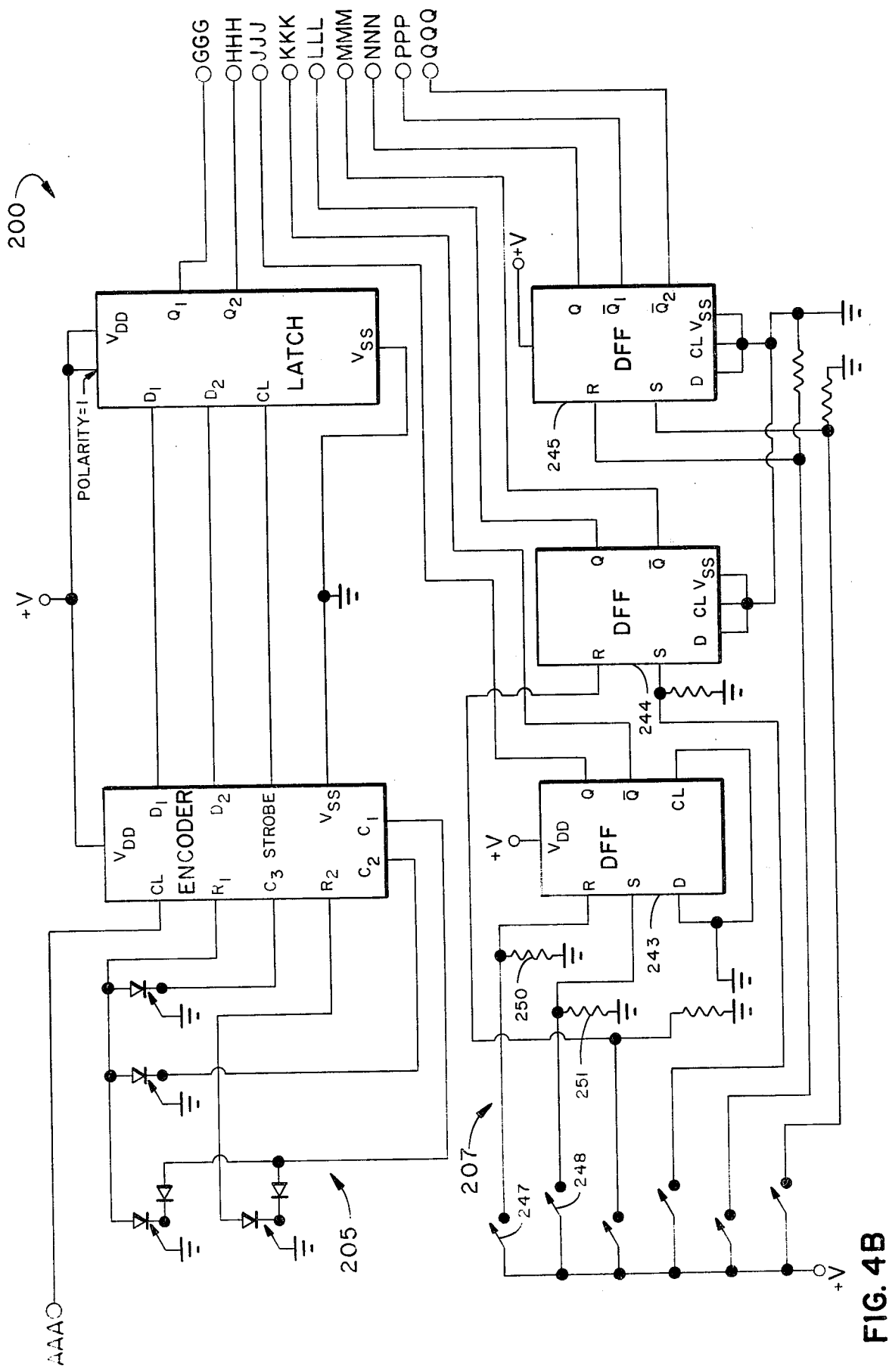
Figure 4C:
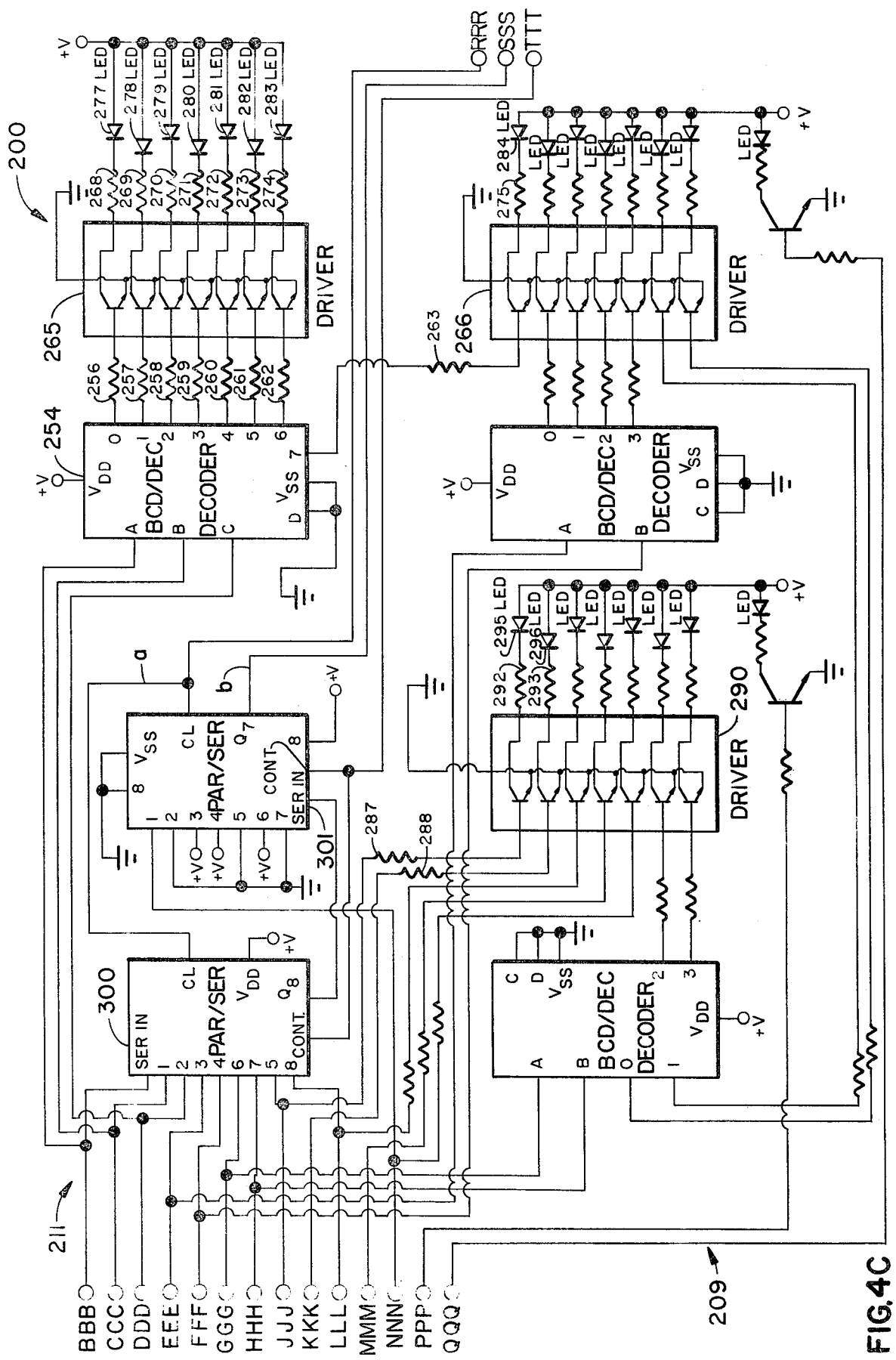
Figure 4D:
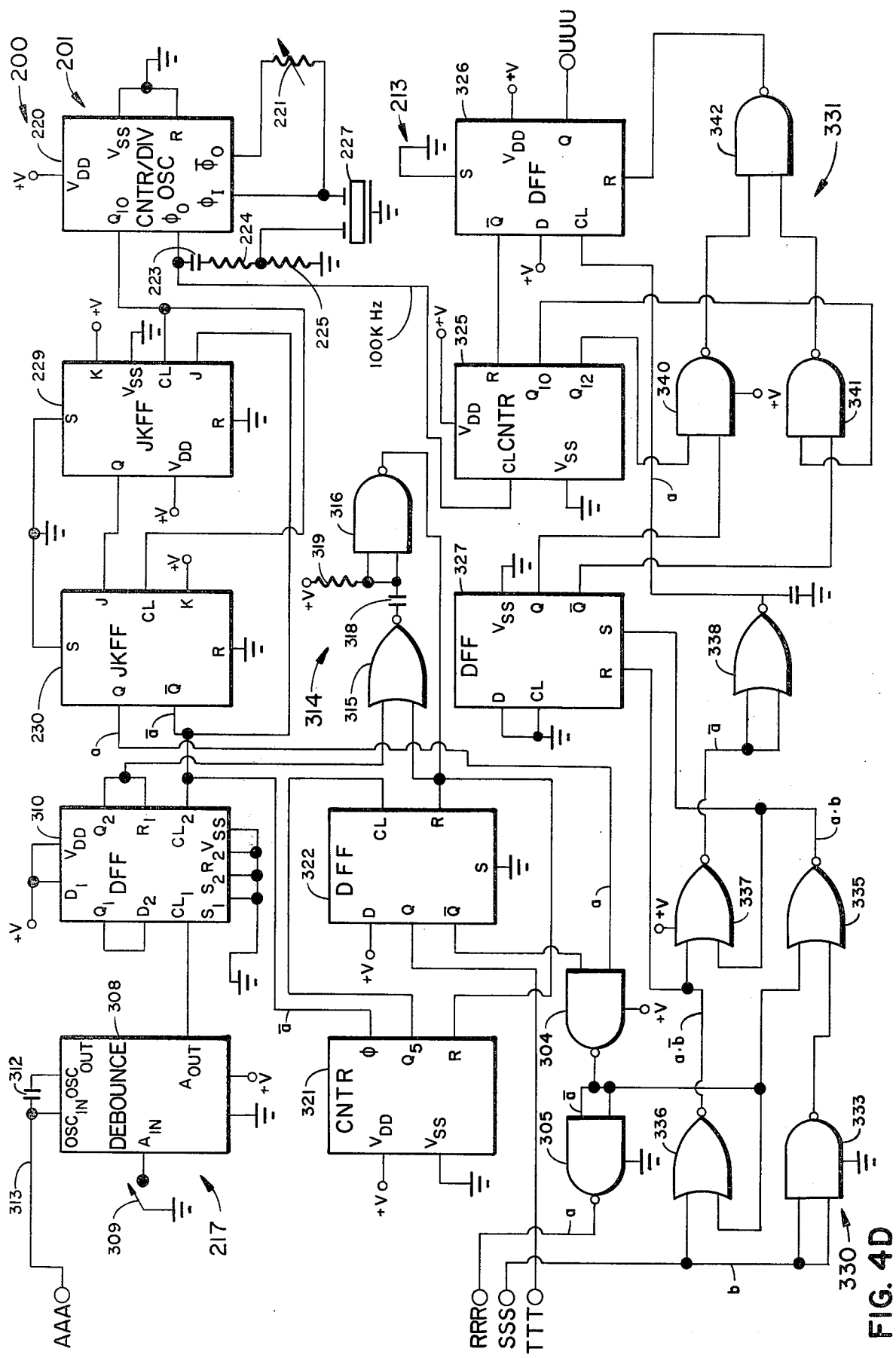

The programmer circuit 200 includes a crystal controlled clock circuit 201 (FIG. 4D) from which the remaining circuitry is driven. The various parameters desired to be controlled are selected by the parameter selector array and latch circuits 204–207 (FIGS. 4A and 4B). The particular parameter selected to be programmed are indicated on respective light emitting diode elements of a display array circuit 209 (FIG. 4C). The selected parameters, in accordance with the parameter selector array and latch circuits 204–207 are conducted to a parallel to serial data converter circuits 211 (FIG. 4C), the serial data being conducted to an output width converter circuit 213 (FIG. 4D) to control a driver circuit 350 (FIG. 4E) for transmission to the implanted pacer. The programmer circuit 200 is initiated in its operation after the various selector switches are operated, as below described, by a synchronizing start and activating circuit 217 (FIG. 4D).

With reference now particularly to the crystal control clock circuit 201, (FIG. 4D) the clock pulses are initiated by a counter/divider and oscillator integrated circuit 220. The $\bar{\phi}_0$ and the $\phi_1$ are interconnected by a variable resistor 221. The $\phi_0$ is connected to ground or low state by a capacitor 223 and two resistors 224 and 225 connected in series. A crystal 227 is connected between the $\phi_1$ terminal of the counter/divider-oscillator 220 and the junction of the voltage dividing resistors 224 and 225, on one side, and to a low state or ground on the other. The values of the components and the crystal are selected to produce a 100 kilohertz output signal upon the $\phi_0$ terminal of the counter/divider-oscillator 220. The reset terminal of the counter/divider-oscillator 220 is connected to a logic low state, or ground, and an output is derived from the $Q_{10}$ output terminal. A frequency divider pair of J-K master-slave flip-flop pair 229 and 230 are provided to receive the output pulses produced on the $Q_{10}$ terminal of the counter/divider-oscillator 220 at their respective clock input terminals. The K terminal of each of the J-K flip-flops 229 and 230 are connected to a logic high state, and the set and reset terminals of each are connected to a logic low state. The Q output of the J-K flip-flop 229 is connected to the J input of the J-K flip-flop 230, and the $\overline{Q}$ output of the J-K flip-flop 230 is connected to the J input of the J-K flip-flop 229. The Q and $\overline{Q}$ outputs of the J-K flip-flop 230 produce clock pulses and inverted clock pulses, respectively, to the remainder of the circuitry 200. For convenience, the signal developed at the Q terminal of the J-K flip-flop 230 is denoted by the letter "a" at various points throughout the circuit diagram, and, the signal developed $\overline{Q}$ terminal is denoted by the letter $\bar{a}$. Thus, the clock circuit 201 produces three outputs: a clock pulse output, a, an inverted clock pulse output, $\bar{a}$, and a 100 kilohertz timing output. The operation of the clock circuit 201 is described in conjunction with the remaining circuitry in further detail below.

The individual parameter selection capabilities are provided by the parameter selector array and latch circuits 204–207 (FIGS. 4A and 4B). For example, the parameter selector array and latch 204 provides the capability of selecting among eight different parameters, which may be employed, for example, to control the rate of the implanted pacer. Thus, for example, eight switches 230–237 (FIG. 4A) may provide a capability of selecting between 50, 60, 70, 80, 90, 100, 110, and 120 beats per minute, respectively, (or other parameters as may be predetermined by appropriate components and connection of the associated pacer).

The switches are connected in an array as shown to a binary encoder 240 through respective isolating diodes. Thus, for example, the switches 230–232 are connected to the R1 input of the encoder 240, switches 233–235 are connected to the R2 input of the encoder, and switches 236 and 237 are connected to the R3 input of the encoder. Likewise, switches 232 and 235 are connected to the C3 input, switches 231, 234, and 237 are connected to the C2 input, and switches 230, 233, and 236 are connected to the C1 input of the encoder 240. Outputs are developed upon the output terminals D1, D2, and D3 to be conducted to the D1, D2, and D3 inputs, respectively, of a latch 241. The latch 241 develops outputs upon its output terminals Q1, Q2, and Q3 in correspondence with the particular one of switches 230–237 which is closed. The clock input to the binary encoder 240 is connected to receive clock pulses from the start circuit 217 (see terminal AAA in FIG. 4D), as described below. Additionally, the encoder 240 has a strobe output which is connected to the clock input of the latch 241, which functions to produce a strobe or clock pulse a predetermined time after the arrival of a clock pulse to the encoder to insure that any switch bounce or the like has subsided.

The parameter selector array and latch circuits 205 and 206 are of similar construction to that of the parameter selector and array latch 204 above described, and are not further described herein in detail other then to note the circuits 205 and 206 have fewer switches then that presented by the circuit 204, and may be used, for example, to control the sensitivity parameter and amplitude parameter of the pacer, respectively. Thus, four sensitivity and four amplitude selections are provided by the respective circuits 205 and 206.

Finally, the parameter selector array and latch circuit 207 (FIG. 4B) provides a capability of three parameter controls in which only two parameter selections are desired for each control.

The parameter selector array latch circuit 207 includes three D-type master-slave flip-flops 243, 244, and 245, each connected to serve as an RS flip-flop. That is, the D and clock inputs of each of the flip-flops 243-245 are connected to a low logic state. The outputs derived at the Q and $\overline{Q}$ terminals are dependent upon the inputs to the R and S terminals of the flip-flop, whereby, for example, when a high state is applied to the reset terminal, the Q and $\overline{Q}$ outputs are zero and one, respectively, and when a high state is applied to the set terminal, the Q and $\overline{Q}$ outputs are one and zero, respectively.

Associated with the flip-flop 243 are two switches 247 and 248 which are connected, respectively, between a high logic state and the reset and set terminals thereof. Resistors 250 and 251 are connected between the reset and set terminals, respectively, to ground, across which the input signal is developed to the reset and set terminals. Thus, a two condition state, such as may correspond to a two width selection parameter, may be provided by the flip-flop 243 in conjunction with the switches 247 and 248. Similarly, the flip-flops 244 and 245 include switches for two parameter selection, in a similar fashion, which is herein not described further in detail.

The outputs from the parameter selector array and latch circuits 204–207 are conducted to the parallel-to-serial data converter circuit 211 (FIG. 4C) as well as the display array 209 (FIG. 4C). The display array 209 includes a number of BCD-to-decimal decoders and driver circuits to respective light emitting diodes (LEDs). The decoder and driver stages for the parameter selector array and latch circuits 204–206 are similar; consequently, only the driver circuit used in conjunction with the parameter selector array and latch circuit 204 is described herein in detail, similar connections and circuit elements being used in conjunction with those of parameter selector array and latch circuits 205 and 206. The outputs from the latch circuit 241 are conducted to the A, B, and C imputs of a BCD-to-decimal decoder 254. The decimal output corresponding to the binary input is produced at the output terminals 0–7, to be conducted via respective resistors 256–263 to respective inputs of driver stages 265 and 266. The outputs from the driver stages 265 and 266 are conducted via respective resistors 268–275 to respective LEDs 277–284.

Thus, in operation, if, for example, switch 234 were closed, which corresponded, for example, to a desired heart beat rate of 100 beats per minute, an output corresponding uniquely to the closure of the switch 234 will be exhibited upon the output terminal D1–D3 of the encoder 240. Upon the occurrence of the strobe pulse following a clock pulse to the encoder, the outputs on the D1-D3 terminals of the encoder 240 would be applied to the latch circuit 241 to produce a corresponding change in state on the output terminals Q1-Q3 thereof. The state change would then be applied to the input terminals A-C of the BCD-to-decimal decoder 254, to produce, for instance, an output corresponding to the switch 234, for instance, at the 6 output terminal. The state change, therefore, would be conducted via the resistor 262 through the driver stage 265, through the resistor 274, to produce a light emitting condition by the LED 283, to thus indicate the rate selected.

The parameter selector array and latch circuit 207 (FIG. 4B) operates slightly differently in conjunction with the display array 209, as follows. The output from the respective flip-flops 243-245 are conducted directly to a driver stage, then to the light emitting diodes. For example, with respect to the flip-flop 243, the outputs Q and $\overline{Q}$ are conducted via resistors 287 and 288 (FIG. 4C) to the driver circuit 290 (FIG. 4C). The respective outputs of the driver circuit 290 are conducted via resistors 292 and 293 to LEDs 295 and 296. The outputs from the flip-flops 244 and 245 are similarly connected to respective dirver circuits (separate transistors being provided, as necessary) to respective resistor and LED indicators.

As mentioned above, in addition to producing a signal to the display array 209, the outputs from the parameter selector array and latch circuits 204-207 are conducted to respective inputs of parallel-to-serial converters 300 and 301 of the parallel-to-serial converter circuit 211 (FIG. 4C). The parallel-to-serial converters 300 and 301 have their clock input terminals connected to receive clock pulses in accordance with the clock pulse signal a from the clock circuit 204 via a NAND gate 304 and a NAND gate 305, (connected as an inverter, as shown in FIG. 4D) as below described. The $Q_8$ output of the parallel-to-serial converter 300 is connected to the serial input terminal of the parallel-to-serial converter 301, whereby as clock pulses are applied to the respective parallel-to-serial converters 300 and 301, the data presented upon the input terminals of the inverter 300 are clocked into the respective register positions of the parallel-to-serial converter 301, to be outputted upon the $Q_7$ output terminal of the parallel-to-serial converter 301. The output data signal from the terminal $Q_7$ of the parallel-to-serial converter 301 is denoted by the letter "b" on the various lines hereinafter described.

In addition to the data presented from the parameter selector array and latch circuits 204-207, seven of the input terminals of the parallel-to-serial data converter 301 are hard-wired to logic states corresponding to the desired access code required to enable the pacer control above described to receive the desired parameter control logic signals. Thus, in the embodiment illustrated, input terminals 2, 5 and 7 are connected to logic low or 0 states, and input terminals 3, 4, 6 and 8 are connected to logic high or 1 states.

Thus, in operation, the signal "b" appearing on the output line $Q_7$ from the initial starting time, is serially the access code hard-wired onto the input terminals 2-8 of the parallel-to-serial converter 301, followed by the data presented upon the input terminal 1 of the parallel-to-serial converter 301 and the input terminals SER IN-8 of the parallel-to-serial converter 300, coinciding with each clock pulse appearing on lines "b" and "a" are conducted to the output width converter circuit 213, below described.

The circuit is activated by the start control circuit 217 (FIG. 4D), which includes a debounce integrated circuit 308, which has a start switch 309 connected to the $A_{in}$ terminal, the output appearing on the $A_{out}$ terminal to a synchronizing pair of D flip-flops in an integrated circuit package 310. A capacitor 312 is connected between the $OSC_{in}$ and $OSC_{out}$ terminals of the debounce circuit 308 to produce clock pulses on an output line 313 from the $OSC_{in}$ terminal to drive the various encoders of the parameter selector array and latch circuits 204-207 as shown, (terminal AAA) and as above described. The D flip-flop pair package 310 receives its clock$_1$ input from the $A_{out}$ terminal of the debounce circuit 308, corresponding to the closure of the start switch 309 after the predetermined delay time of the debounce circuit. The $D_1$ terminal is connected to a high state, and the $Q_1$ output is connected to the $D_2$ input. The $Q_2$ output is connected to the reset terminal of the first flip-flop ($R_1$), and the clock input of the second flip-flop ($CL_2$) receives the "ā" clock pulses from the clock circuit 201. Thus, the output derived upon the output terminal $Q_2$ of the D flip-flop package 310 is synchronized with the clock pulses on the clock pulse line "ā" after the closure of the start switch 309, and the debounce delay provided by the debounce circuit 308.

The $Q_2$ output of the D flip-flop package 310 is conducted to a one-shot multivibrator circuit 314 (FIG. 4D), including a NOR gate 315 and a NAND gate 316, connected as an inverter, the inputs of which are connected to the output of the NOR gate 315 by a capacitor 318. The output of the NAND gate 316 is conducted to one input of the NOR gate 315, and the $Q_2$ output of the D flip-flop 310 is connected to the other input thereof. A resistor 319 is connected between the inputs of the NAND gate 316 and a high logic state to provide in conjunction with the capacitor 318 an RC time constant to control the width of the pulse produced by the one-shot multivibrator 314.

The output from the NAND gate 316 is connected to the reset terminals of a counter 321 and a D-type master-slave flip-flop 322 (FIG. 4D), which serve as a start enable circuit, to function as follows. The clock input of the counter 321 is connected to the clock generator 201 to receive the "ā" clock signal produced at the $\overline{Q}$ output of the J-K flip flop 230. The $Q_5$ output terminal of the counter 321 is connected to the clock terminal of the D flip-flop 322. The D input terminal of the D flip-flop 322 is connected to a high logic state, and the $\overline{Q}$ output terminal is connected to an input terminal of the NAND gate 304 to control the passage therethrough of the "a" clock signal from the clock circuit 201. The Q output terminal of the D flip-flop 322 is connected to the control terminals of the parallel-to-serial converters 300 and 301 (FIG. 4C) to cause them to operate in a serial output mode. Thus, in operation, when the start switch 309 (FIG. 4D) is depressed, the debounce effects which may exist are eliminated by the debounce circuit 308. The D flip-flop pair 310 produces an output synchronized with the "ā" clock signal to activate the one-shot multivibrator circuit 314. The normally high state existing on the NAND gate 316 is changed to a low state during the period of the one-shot multivibrator 314, thereby enabling the counter 321 and the D flip-flop 322 to operate. After the delay prescribed by the counter 321, the outputs Q and $\overline{Q}$ of the D flip-flop 322 are changed to begin the operation of the parallel-to-serial converters 300 and 301 (FIG. 4C) and to permit the passage of the clock pulses through the NAND gate 304 (FIG. 4D). Thus, appearing at the inputs to the output width converter circuit 213 on the line "b" and "$\bar{a}$" are the serial data and the "$\bar{a}$" clock signals, respectively.

The output width converter circuit 213 (FIG. 4D) includes a counter 325 and two D-type flip-flops 326 and 327. An input logic network 330 is provided to control the D flip-flop 326 and 327, and an interconnecting logic network 331 is provided between the D flip-flop 327 and counter 325 also to control the D flip-flop 326.

More specifically, the input logic network 330 includes a NAND gate 333 connected as an inverter and four NOR gates 335–338, the NOR gate 338 also being connected as an inverter. The "b" signal from the output of the parallel-to-serial converter 301 is conducted to the NAND gate 333 and to one input of the NOR gate 336. The output from the NAND gate 333 is conducted to one input of the NOR gate 335, and the "$\bar{a}$" clock signal at the output of the NAND gate 304 is connected to the other terminals of the NOR gates 335 and 336. The outputs of the NOR gates 335 and 336 are connected to respective inputs of the NOR gate 337, the output of which is inverted by the NOR gate 338 to be applied to the clock input of the D flip-flop 326. Additionally, the output from the NOR gate 336 is connected to the reset terminal of the D flip-flop 327 and the output of the NOR gate 335 is connected to the set terminal of the D flip-flop 327. It can therefore be seen that the signal applied to the clock input of the D flip-flop 326 corresponds to the "a" clock signal. The signal applied to the reset terminal of the D flip-flop 327 corresponds to the "a·$\bar{b}$" signal and the signal applied to the set terminal of the D flip-flop 327 corresponds to the "a·b" signal. Thus the outputs Q and $\bar{Q}$ are 1 and 0 respectively, for a logic one data pulse and are 0 and 1 respectively, for a logic zero data pulse (both in conjunction, of course, with the clock pulse "a").

The counter 325 receives its clock pulses from the 100 kilohertz output of the clock circuit 201, and produces outputs at its $Q_{10}$ and $Q_{12}$ output terminals. The reset terminal is connected to the $\bar{Q}$ output of the D flip-flop 326.

The interconnecting logic network 331 includes three NAND gates 340–342 interconnected as follows. The Q output of the D flip-flop 327 is connected to one input of the NAND gate 340, and, in a similar fashion, the $\bar{Q}$ output is connected to one input of the NAND gate 341. The $Q_{12}$ output of the counter 325 is connected to the other input terminal of the NAND gate 340, and the $Q_{10}$ output of the counter 325 is connected to the other input of the NAND gate 341. The outputs of the NAND gates 340 and 341 are connected to the respective inputs of the NAND gate 342. The output of the NAND gate 342 is connected to the reset terminal of the D flip-flop 326.

Thus, in operation, there is a change in state upon the output terminals $Q_{10}$ and $Q_{12}$ of the counter 325 after 5.1 milliseconds and 20.5 milliseconds, respectively. Additionally, as above indicated, the Q and $\bar{Q}$ states of the D flip-flop 327 are zero-one or one-zero respectively for logic states zero or one of the "b" signal. Thus, the coincidence of the high Q state of the D flip-flop 327 and the high $Q_{12}$ state of the counter 325 produces a resetting signal at the output of the NAND gate 342 after 20.5 milliseconds. Similarly, the coincidence of the high $\bar{Q}$ state of the D flip-flop 327 and the high $Q_{10}$ state of the counter 325, corresponding to a zero data state, produce a resetting state at the output of the NAND gate 342 after 5.1 milliseconds. Thus, since the D flip-flop 326 is clocked by the "a" clock signal, the Q output of the D flip-flop 326 (the D input being tied high) will be of width 5.1 milliseconds for a "zero" data pulse ("b") and of 20.5 milliseconds for a "one" data pulse ("b").

Figure 4E:
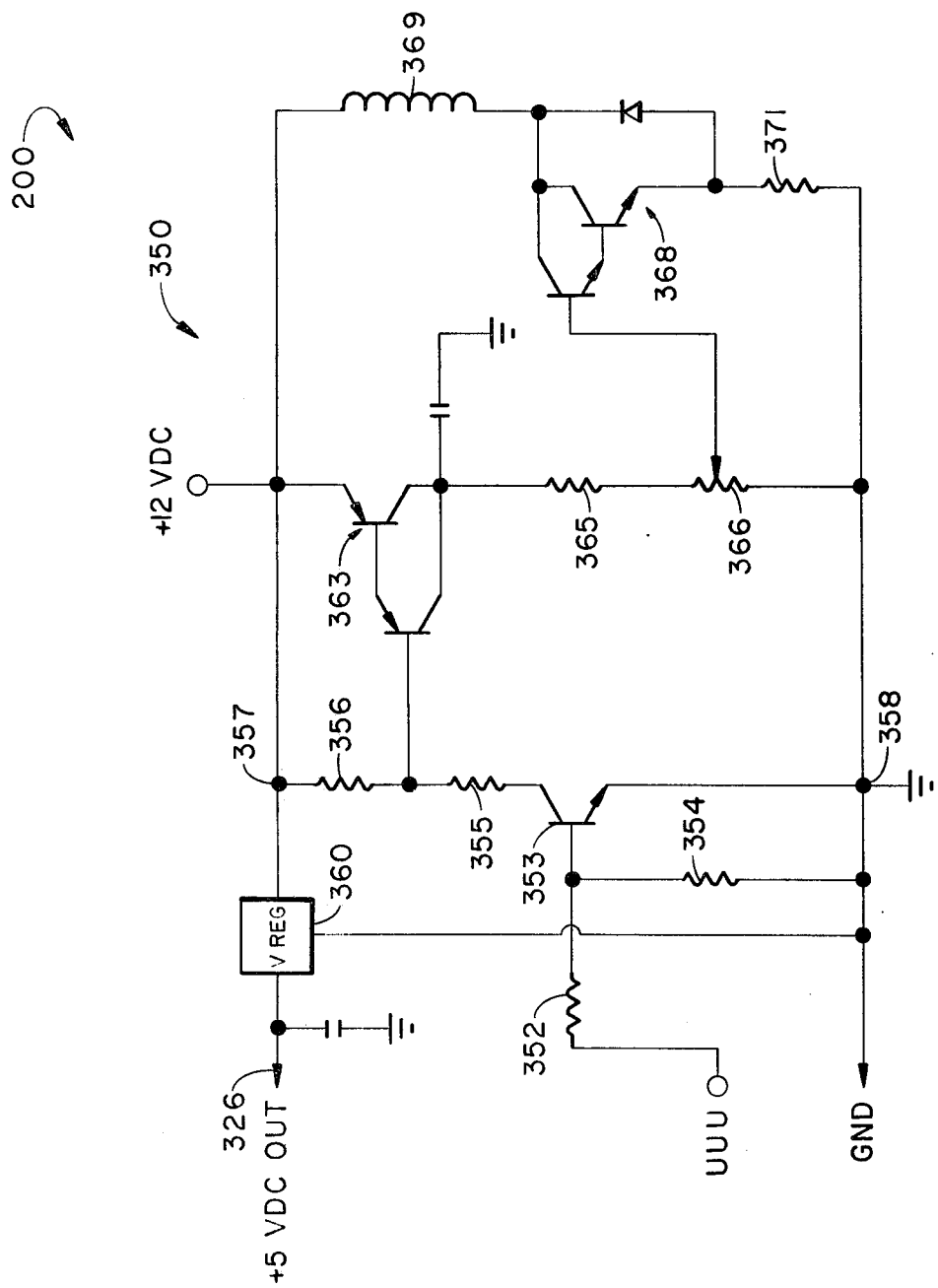

The output upon the Q terminal of the D flip-flop 326 is connected to the coil driver circuit 350, shown in FIG. 4E. The Q output from the D flip-flop 326 is connected through a series resistor 352 to the base of an npn transistor 353. The collector of the transistor 353 is connected via series resistors 355 and 356 to a positive bus 357, and the emitter is connected to the negative bus 358. A resistor 354 is connected between the base of the transistor 353 to ground. The voltage between the positive bus 357 and negative bus 358 is controlled by a voltage regulator circuit 360, which may be, for example, an MC 7805 integrated circuit. A positive source of voltage (not shown) is applied to the terminal 362, and the negative bus 358 is connected to ground.

The signal developed upon the resistor 355 is connected to a Darlington transistor pair 363 to develop an output voltage upon resistors 365 and 366. The resistor 366 is a variable resistor, with the output taken from an armature thereof to be applied to a second Darlington transistor pair 368. An electromagnet 369 is connected between the positive bus 557 and the collector of the top transistor of the Darlington pair 368. A small resistor 371 is connected between the emitter of the lower transistor of the Darlington pair 368 and the ground bus 358.

Thus, as the serial data of pulses of widths of 5.1 milliseconds and 20.5 milliseconds is applied to the circuit, the electromagnet 369 produces magnetic pulses for transmission to the implanted pacer control circuit, in accordance therewith, for controlling the parameters of the pacer as above described.

It should be noted that the control circuit of the programmer 20 has been illustrated with 22 different states or conditions for parameter selection. Larger or fewer control states could easily be employed, the particular number illustrated being used to fully complement the control circuit 51 above described in detail with reference to FIGS. 3A–3C particularly.

Although the invention has been described and illustrated with a certain degree of particularity, it is understood that numerous changes in the arrangement and combination of parts may be resorted to without departing from the spirit and scope of the invention as hereinafter claimed.

We claim:
1. A heart pacer comprising:
a heart pacer having controllable parameters adapted to be implanted within a patient,
means for receiving a set of pulses of selected individual widths, applied externally of the patient, the individual widths of each of the received pulses representing a binary logic state of zero or one, the binary logic states of said set of pulses representing a corresponding set of controllable parameters,
means for decoding the received pulses in accordance with the individual width of each of the received pulses including, a reference pulse generator for producing a series of pulses each in timed relation to a respective one of said received magnetic pulses, and pulse comparison means operative to detect each received pulse as a zero or one in dependence upon the time of coincidence between the received pulse and its respective reference pulse, and means into which said decoded received pulses are registered for controlling the controllable parameters of said heart pacer in accordance with the logic states represented by said received pulses.

2. The circuit of claim 1 further comprising locking means for counting said received pulses to provide a signal to said means for controlling said control parameters to allow registering therein of said logic states only upon the reception of a predetermined number thereof.

3. The circuit of claim 2 further comprising means for recognizing a preselected plurality of said received pulses defining an access code and for producing logic states of zero or one in correspondence with the respective widths of said preselected plurality of said pulses, latch means for controlling the application of the remaining of said received pulses to said means for controlling said controllable parameters, and means for recognizing a predetermined pattern of said logic states produced in correspondence with said preselected plurality of said received pulses and to which said logic states are applied for controlling said latch means.

4. The circuit of claim 3 further comprising means to which said received pulses are applied to disable after a preset time said means for recognizing a preselected plurality of said received pulses.

5. A heart pacer, comprising:

a heart pacer having controllable parameters adapted to be implanted within a patient;

a circuit for providing parameter control states to said heart pacer, comprising:

means connected to said pacer for receiving a set of externally applied pulses each of first or second width representing logic zero and logic one, respectively;

means for generating timing pulses having a period longer than the width of those of said pulses representing a logic zero and shorter than the width of those of said pulses representing a logic one;

and register means to a data input of which said received pulses are applied and to a clock input of which said timing pulses are applied to thereby produce zero and one logic states in said register as parameter control states to said pacer.

6. The circuit of claim 5 further comprising:

a control logic presenting latch for receiving the parameter states from said register, and means for counting said received pulses connected to said register means for allowing the transfer to the control logic presenting latch of said zero and one logic states only if a preselected count is received.

7. The circuit of claim 6 further comprising latch circuit means for receiving said logic states from said register means, and means for activating said latch means after said register means is disabled.

8. The circuit of claim 6 further comprising means for recognizing an access code among said received pulses and for disabling said production of logic states within said register means until said access code is recognized.

9. The circuit of claim 8 wherein said access code recognizing means comprises second register means to a data input of which said received pulses are applied and to a clock input of which said timing pulses are applied to thereby produce zero and one logic states therein to be recognized as said access code.

10. A heart pacer of the type having variable and controllable operating parameters adapted to be implanted within a patient comprising:

pulse generating means adapted to deliver stimulation pulses to the patient's heart;

means for receiving a set of magnetic pulses each of selected width, applied externally from the patient;

means for generating timing pulses of predetermined fixed width, each timing pulse occurring in timed relationship with said received magnetic pulses, to be associated with a respective one of said received pulses;

means for comparing the coincidence between each of said received pulses and the associated timing pulse and for detecting each of said received magnetic pulses as representing a first logic state in correspondence with said coincidence exceeding a first time period and as representing a second logic state in correspondence with said coincidence not exceeding said first time period;

means onto which said detected logic states are registered for presenting said logic states as parameter control states;

and means interconnecting said pulse generating means and said logic states presenting means to vary and control the operating parameters of said stimulation pulse generating means in correspondence with said logic states.

11. A heart stimulation circuit adapted to be fully implanted in a patient, comprising;

a demand heart pacer of the type having operating parameters variable in correspondence with predetermined logic states, adapted to deliver stimulation pulses to and receive naturally occurring heart pulses from the patient's heart;

means for receiving a set of externally transmitted magnetic pulses, each pulse being either of first width representing a logic zero or of second width representing a logic one;

means for registering logic states of zero and one in accordance with the logic representations of said received pulses;

and means interconnecting said demand heart pacer and said registering means to vary the operating parameters of said demand heart pacer.

12. The heart stimulation circuit of claim 11 wherein said interconnecting means comprises a control logic presenting latch, and further comprising means for counting said received pulses for allowing the transfer from said registering means to the control logic presenting latch of said logic states only if a predetermined number of pulses are received.

13. The heart stimulation circuit of claim 12 further comprising timing means to generate a signal a predetermined time after the beginning of the reception of said pulses to control said interconnecting means to apply said logic states to said demand heart pacer only after said predetermined time.

14. The heart stimulation circuit of claim 11 further comprising means for generating timing pulses at a period greater than the width of said received pulses of first width and less than the width of said pulses of second width, and wherein said registering means is a register to a data input of which said received pulses are applied and to a clock input of which said timing pulses are applied, whereby logic states of zero and one are registered in said registering means in accordance with the widths of said received pulses.

15. The heart stimulation circuit of claim 14 further comprising:
- second registering means to a data input of which said received pulses are applied and to a clock input of which said timing pulses are applied,
- gate means to produce a logic state change only when a predetermined logic combination is registered in said second registering means, and
- enable means connected to permit the application of said received pulses to said first registering means, said enable means being activated by said logic state change of said gate means.

* * * * *